United States Patent [19]

Kumada et al.

[11] Patent Number: 5,000,579
[45] Date of Patent: Mar. 19, 1991

[54] FROST AND DEW SENSOR

[75] Inventors: Akira Kumada, Yokohama; Eiichi Takata, Nagaokakyo; Michihiro Murata, Kyoto, all of Japan

[73] Assignee: Murata Mfg. Co., Ltd., Japan

[21] Appl. No.: 553,740

[22] Filed: Jul. 18, 1990

Related U.S. Application Data

[62] Division of Ser. No. 420,600, Oct. 21, 1989.

[30] Foreign Application Priority Data

Oct. 20, 1988 [JP] Japan .................. 63-264842
Oct. 28, 1988 [JP] Japan .................. 63-272435

[51] Int. Cl.$^5$ .............................. G01N 25/66
[52] U.S. Cl. .......................... 374/28; 374/16; 374/10
[58] Field of Search .......... 374/10, 11, 28, 16; 73/336.5; 364/557

[56] References Cited

U.S. PATENT DOCUMENTS

| | | | |
|---|---|---|---|
| 2,904,995 | 9/1959 | Obermaier | 374/28 |
| 3,514,993 | 6/1970 | Simpson | 374/16 |
| 4,579,462 | 4/1986 | Rall et al. | 374/28 |
| 4,586,828 | 5/1986 | Winter et al. | 374/16 |

FOREIGN PATENT DOCUMENTS

| | | | |
|---|---|---|---|
| 0035220 | 2/1989 | Japan | 374/10 |
| 0315108 | 9/1971 | U.S.S.R. | 374/10 |
| 0325548 | 1/1972 | U.S.S.R. | 374/10 |
| 0928206 | 5/1982 | U.S.S.R. | 374/28 |
| 1260805 | 9/1986 | U.S.S.R. | 374/28 |
| 1409910 | 7/1988 | U.S.S.R. | 374/10 |

OTHER PUBLICATIONS

Du Pont 900 Differential Thermal Analyzer, Instrument Products Division, Wilmington, DE (Jun. 1963).

Primary Examiner—William A. Cuchlinski, Jr.
Assistant Examiner—Diego F. F. Gutierrez
Attorney, Agent, or Firm—Oliff & Berridge

[57] ABSTRACT

In a frost and dew sensor composed of two thermosensitive resistors, a power source and an arithmetic circuit, frost or dew is detected from the change of a differential temperature between the two thermosensitive resistors as two different currents from the power source are supplied to the respective thermosensitive resistors. In an alternative form, the sensor has a single thermosensitive resistor, which is energized as two different currents are alternately supplied from the power source so that frost or dew is detected by comparison of the time-lags between the two outputs from the thermosensitive resistor.

8 Claims, 11 Drawing Sheets

OSCILLATION OUTPUT OF RESONANCE-FREQUENCY VARIABLE TYPE

OSCILLATION OUTPUT OF RESONANCE-AMPLITUDE VARIABLE TYPE

DETECTION OUTPUT

FROST AND DEW SENSOR

This is a division of application Ser. No. 07/420,600 filed Oct. 12, 1989.

BACKGROUND OF THE INVENTION

1. Field of the Invention

This invention relates to a frost and dew sensor for use in a defroster of a refrigerator, air-conditioner and various other industrial appliances.

2. Description of the Related Art

It has been a common knowledge that under certain conditions, the surface of a heat-exchanger, incorporated in a refrigerator, an air-conditioner or a similar apparatus, is covered with frost and ice. Continued operation of the heat-exchanger covered with frost and ice would remarkably reduce the energy efficiency, which is uneconomical and occasionally causes a failure or fault.

Heretofore, attempts were made to detect the building-up of frost and dew; some of the proposed detecting means used a resonator, some utilized the change of dielectric constant of an element due to the developing of frost or dew, and others were optical type.

FIGS. 13 through 16 of the accompanying drawings illustrate two prior art sensors each using a resonator; one sensor detects the change of resonance frequency of a resonator, and the other detects the change of amplitude of a resonator.

In FIG. 13, a piezo-electric resonator 14 is supported on the upper surface of a tubular housing 10 via a resilient support 12 and bears a pair of electrodes 16a, 16b attached one on each side of the resonator 14, and a pair of output terminals 18a, 18b leading from the electrodes 16a, 16b, respectively.

FIG. 14 is a circuit diagram of the sensor of FIG. 13, in which the output of the resonator 14 is supplied to a resonance-frequency discriminator 22 via a resistor R on one side and an amplifier 20 on the other side where the output is amplified as a matter of fact. Then the output of the discriminator 22 is taken out to the exterior. In operation, as frost or dew develops over the surface of the resonator 14, the resonance frequency derived from the resonator 14 varies depending on the amount of frost or dew built up. When the extent of change in resonance frequency climbs over a predetermined value, this sensor discriminates or judges that the resonator 14 has been covered with frost or dew.

The sensor of FIG. 15 is of the type in which the developing of frost or dew is detected based on the change of amplitude of a resonator 114. This sensor is identical in basic construction with that of FIG. 13; but, the output of the resonator 114 is supplied to an oscillation amplitude discriminator 124, as shown in FIG. 16. In this sensor, as frost or dew develops over the surface of the resonator 114, the oscillation of the resonator 114 is restricted depending on the weight of frost or dew grown up. Thus when the extent of change in amplitude ascends beyond a predetermined value, this sensor presumes that the surface of the resonator 114 has been covered with frost or dew.

FIGS. 17 to 19 are diagrams showing various wave forms of the oscillation outputs of the piezo-electric resonator 114 and of the detected outputs of the sensors shown in FIGS. 13 through 16.

Specifically, FIG. 17 shows a wave form of the oscillation output of the sensor of FIGS. 13 and 14, indicating that at a time point $t_1$, concurrently with the developing of frost, the resonance frequency increased about two times. FIG. 18 shows another wave form of the oscillation output of the sensor of FIGS. 15 and 16; it can be observed that concurrently with the developing of frost or dew (time point $t_1$), the amplitude of the output signal derived from the resonator 114 is reduced.

When any change of the oscillation frequency or amplitude has thus been found, the sensor outputs a signal giving a notice that the resonator 14, 114 has been covered with frost or dew, in response to which generally a defroster or a dehumidifier is energized.

FIGS. 20 to 22 illustrate another prior art sensor of the type utilizing the change of dielectric constant to detect frost and dew. FIGS. 20 and 21 show the inside structure and outside appearance, respectively, of the sensor; a resistor film 230 is coated over the surface of an insulating substrate 228 on which a pair of comb-shaped electrodes 226, 226 is printed. FIG. 22 shows a detector circuit of the sensor; an alternating voltage from an alternating signal source 134 is impressed to a detection unit 232 having the construction of FIGS. 20 and 21, and the output of the detection unit 232 is supplied to an impedance detector circuit 236, the output terminal of which is connected to a non-illustrated defroster or dehumidifier.

With this prior arrangement, as frost or dew develops over the surface of the detection unit 232, the alternating impedance between the two comb-shaped electrodes 226, 226 varies. When the impedance detector circuit 236 detects this change in the impedance, it presumes that the surface of the detection unit 232 has been covered with frost or dew.

FIGS. 23 and 24 illustrate an optical type of prior art sensor.

Specifically, FIG. 23 shows the principle of operation of the sensor having a light-emitting element 338 and a light-receiving element 340; light from the light-emitting element 338 reflects on a reflection surface 342 and then strikes on the light-receiving element 340. As frost or dew develops over the reflection surface 342, the refractive index of the light from the light-emitting element 338 or the angle of incidence of the light falling on the light-receiving element 340 deviates so that the amount of light falling on the light-receiving element 340 is reduced. When any change of the light amount is thus found, the sensor makes a judgment that the surface of the reflection surface 342 has been covered with frost or dew.

FIG. 24 show the principle of operation of the sensor having an LED (light-emitting diode) 438 and a photodiode 440 receptive of the light from the LED 438. As frost or dew develops on a path of light spanning between the LED 438 and the photodiode 440, the amount of light to reach the photodiode varies. When the extent of change in the light amount is compared with a reference value in a level discriminator 444 and is thus found over the reference value, the level discriminator 444 issues a notice that the path of light between LED 438 and the photodiode 440 has been at least partly blocked by frost or dew grown up.

With the foregoing prior arrangement, the following problems are unavoidable so that adequate usefulness cannot be achieved.

Each of the known sensors of FIGS. 13 through 16, in which a piezo-electric resonator is used, tends to operate incorrectly due to the dust or other foreign matter stuck to the resonator or due to vibrations exerted on the resonator interiorly and exteriorly of the sensor.

In the known sensors of FIGS. 20 through 24, some utilizing the change in dielectric constant and others adopting an optical method, partly since it is difficult to reduce the detection unit into a compact size, and partly since the circuit structure is too complex, maintenance on a periodical basis is essential to keep the detection precision at a predetermined level. Accordingly, it is difficult not only to achieve reproducibility, but also to reduce the cost of production.

SUMMARY OF INVENTION

It is therefore an object of this invention to provide a frost and dew sensor which is compact in size and hence inexpensive to manufacture and which is excellent in both detection precision and reproducibility.

According to a first aspect of this invention, there is provided a frost and dew sensor comprising: a pair of thermosensitive resistors disposed adjacent to each other, each of the thermosensitive resistors being capable of generating heat by itself due to a given current supplied thereto, each thermosensitive resistor having a resistance varying according to the change of temperature of each thermosensitive resistor; a power source for creating a differential temperature between the thermosensitive resistors, the power source including a heat-generating current source for supplying a heat-generating current to one of the thermosensitive resistors, and a comparative reference current source for supplying a comparative reference current to the other thermosensitive resistor so as to cause a temperature increase of the other thermosensitive resistor to only a negligible extent with respect to the temperature increase of the one thermosensitive resistor due to the heat-generating current; and an arithmetic circuit for fetching a temperature at a respective one of the thermosensitive resistors as an output voltage corresponding to the resistance of the respective thermosensitive resistor and for generating a frost-and-dew signal according to a difference in output voltage between the pair of thermosensitive resistors.

In this first arrangement, in air, one thermosensitive resistor receptive of a current supplied from a heat-generating current source is kept at a temperature higher than the temperature of the other thermosensitive resistor receptive of a current normally supplied from a comparative reference current source.

When frost or dew develops over these two thermosensitive resistors located adjacent to each other, heat radiation, from the one thermosensitive resistor kept at a high temperature due to a relatively large current from the heat-generating current source, occurs via the frost or dew developed over the surface of that one thermosensitive resistor. This is because either solid (frost) or liquid (dew) has a heat conductivity larger than air, i.e., gas. As a result, the temperature of the one thermosensitive resistor descends to reduce a differential temperature with respect to the other thermosensitive resistor kept at a substantially constant temperature due to a current supplied from the comparative reference source.

The arithmetic circuit calculates the differential temperature created between the two thermosensitive resistors; when this differential temperature satisfies specified conditions, the arithmetic circuit makes a judgment that the surfaces of the thermosensitive resistors have been covered with frost or dew, and outputs a frost-and-dew signal.

The arithmetic circuit may include a comparator circuit which is composed of two comparators, for example. One of the comparators compares the respective output signals of the thermosensitive resistors with one another, and the other comparator compares the output signal of the one comparator with a reference value.

Further, the arithmetic circuit may be equipped with a freezing level detector circuit for comparing the output of the other thermosensitive resistor corresponding to the comparative reference current with a predetermined freezing level reference value to detect only the developing of frost. The arithmetic circuit may also be equipped with a discriminator for comparing the output of the comparator circuit with the output of the freezing level detector circuit.

The frost-and-dew signal may be outputted through an output circuit where this signal is amplified. The sensor may use a shaft for carrying thereon the individual thermosensitive resistor, and a base supporting the shaft.

The arithmetic circuit should by no means be limited to the analog type. That is, in an alternative form, the output of the individual thermosensitive resistor may be converted between analog form and digital form by an A/D converter, then a differential temperature may be calculated by a $\mu$-CPU, and finally a frost-and-dew signal may be outputted based on the arithmetical result.

The individual thermosensitive resistor may be a thermistor or a resistor made from platinum or nickel.

According to a second aspect of this invention, there is provided a frost and dew sensor comprising: a thermosensitive resistor capable of generating heat by itself due to a given current supplied thereto, said thermosensitive resistor having a resistance varying according to the change of temperature of said thermosensitive resistor; a power source for changing the temperature of said thermosensitive resistor periodically, said power source including a variable constant-current source for alternately supplying a heat-generating current and a comparative reference current to said thermosensitive resistor, said comparative reference current being such that it causes a temperature increase of said thermosensitive resistor to only a negligible extent with respect to the temperature increase due to the heat-generating current; and an arithmetic circuit for fetching a temperature of said thermosensitive resistor as an output voltage according to a resistance corresponding to the temperature and for generating a frost-and-dew signal according to a difference between the output voltage during the heat-generating current is being supplied to said thermosensitive resistor and the output voltage during the comparative reference current is being supplied to said thermosensitive resistor.

In this second arrangement, the arithmetic circuit may include an amplifier for amplifying the output voltage of said thermosensitive resistor, during the comparative reference current is being supplied thereto, a holding circuit for holding the output of said amplifier to output the same output with a delay for the duration the comparative reference current is being supplied to said thermosensitive resistor, and a comparator circuit for comparing a differential temperature, between the output of said holding circuit and the output voltage of said thermosensitive resistor during the heat-generating current is being supplied, with a predetermined reference value.

Further, the power source may be equipped with a timing circuit including an oscillator for producing an alternate timing to alternate the output of said variable constant-current source between the comparative reference current and the heat-generating current. Each of the amplifier and an output circuit similar to that of the first arrangement may be equipped with a switch adapted to be energized and deenergized by the timing circuit.

It is also particularly useful when additional parts similar to those of the first arrangement are incorporated in this second arrangement.

To sum up, according to this invention, since the developing of frost or dew is judged in terms of temperature, occurrence of any misdetection due to dust or other foreign matter stuck on the surface of a detection unit can be reduced to a minimum. Further, since at least one thermosensitive resistor, which is small in size and inexpensive, is used, it is possible to achieve a frost and dew sensor which can be manufactured at a reduced cost and can offer an improved performance.

The above and other objects, features and additional advantages of this invention will become manifest to those versed in the art upon making reference to the detailed description and the accompanying drawings in which a variety of preferred structural embodiments incorporating the principle of this invention are shown by way of illustrative example.

DETAILED DESCRIPTION

Various preferred embodiments of this invention will now be described with reference to the accompanying drawings. A thermistor is used here as a thermosensitive resistor.

Figure 1:
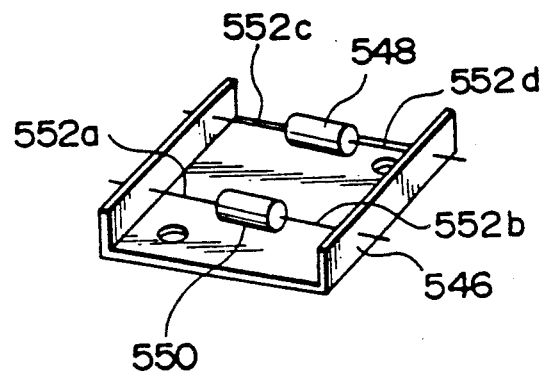
FIG. 1 is a perspective view showing a partial appearance of a frost and dew sensor according to a first embodiment of this invention, in which a pair of thermosensitive resistors is located adjacent to each other.

FIG. 1 shows a partial appearance of a frost and dew sensor (hereinafter also called "sensor") according to a first embodiment of this invention.

In the sensor of the first embodiment, the developing of frost or dew can be judged or discriminated in terms of a differential temperature created between a pair of thermosensitive resistors. In the illustrated example, the sensor comprises a pair of thermosensitive resistors 548, 550 disposed parallel to each other. These two thermosensitive resistors 548, 550 are carried on a pair of shafts 552a and 552b, or 552c and 552d, respectively, supported between opposite side walls of a base 546 with a constant distance between the shafts. In this embodiment, a thermistor having a resistance of 5 kΩ at a B constant of 3350 and 25° C. is used for each of the thermosensitive resistors 548, 550. The heat radiation of the thermistor is 2 mW/ C in air and about 50 mW/°C. in ice. Further, the thermistor offers a resistance of 14 kΩ at 0° C.

Figure 2:
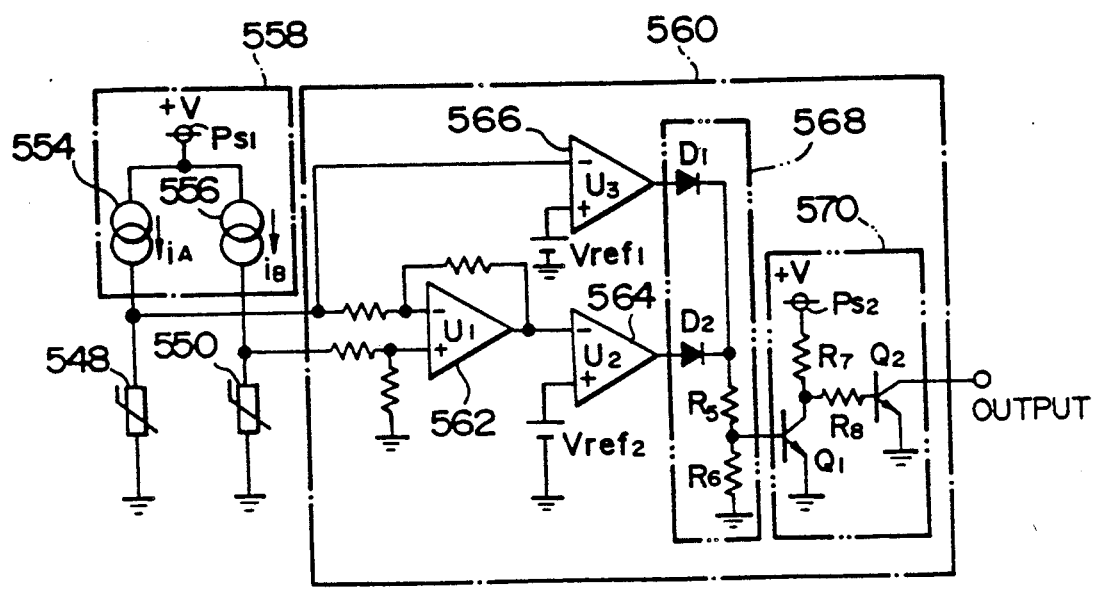
FIG. 2 is a circuit diagram of the sensor of the first embodiment.

FIG. 2 shows the entire circuit of the sensor of this invention, in which the thermosensitive resistors 548, 550 are grounded at one end, and currents are supplied from a power source Ps to the thermosensitive resistors 548, 550 via a pair of constant-current variable circuit 554, 556, respectively, in which different output current values are preset.

These two constant-current variable circuits 554, 556 jointly constitutes a power source 558.

The thermosensitive resistors 548, 550 and the power source 558 are connected to an arithmetic circuit 560 which outputs a frost-and-dew signal in a manner described blow.

The respective outputs of the constant-current variable circuits 554, 556 are supplied to an operational amplifier 562 where a differential temperature between the thermosensitive resistors 548, 550 is calculated. The calculated differential temperature is supplied to one input terminal of a comparator 564 where a judgment is made on whether the differential temperature is below a direct-current reference voltage $Vref_2$.

Meanwhile, the comparator 566 monitors a temperature of the thermosensitive resistor 548 and compares the monitored temperature with a direct-current current reference voltage $Vref_1$ to discriminate whether the monitored temperature is below a reference value.

By this comparison, it is possible to detect the developing of frost only, i.e., apart from the developing of dew, provided that the reference voltage $Vref_1$ is preset to a value equivalent to that at 0° C.

Each of the comparators 564, 566 issues an output only when either the differential temperature value or the monitored temperature value is below a reference value. In the illustrated example, this output is negative logic; a base current flows to a transistor $Q_2$ to render the transistor conductive only when these two outputs meet, the transistor $Q_2$ being included in an output circuit 570.

A transistor $Q_1$ is deenergized only when the two outputs meet. At that time a voltage is impressed from a power source $Ps_2$ to the transistor $Q_2$ via resistances $R_7$, $R_8$ to energize the transistor $Q_2$. As thus energized, the transistor $Q_2$ outputs an open collector signal giving a notice of the developing of frost or dew.

The operation of the sensor according to the first embodiment will now be described.

Figure 3:
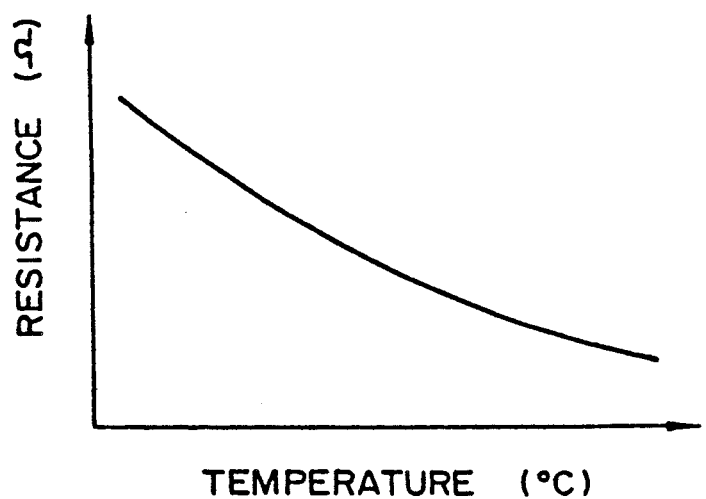
FIG. 3 is a characteristic curve graph showing the general relation between the temperature and resistance of a thermosensitive resistor.

In general, a thermosensitive resistor has a temperature-resistance characteristic such as shown in FIG. 3; temperature and resistance are virtually in reverse proportion to each other.

In FIG. 2, to the one thermosensitive resistor 548, a feeble direct current (i.e., comparative reference current) $i_4$, such that a temperature increase due to the self-heat-generation is negligible, is supplied from a power source $Ps_1$ via the constant-current variable circuit 554. To the other thermosensitive resistor 550, another direct current (i.e., heat-generating current) $i_b$, such that a temperature increase is constant, is supplied from the common power source via the constant-current variable circuit 556. In this case, assuming that the temperature increase of the thermosensitive resistor 550 is $\Delta T$, this $\Delta T$ is determined from an amount of electric power consumed by the thermosensitive resistor 550 and an amount of heat energy (Qr) radiated from the same thermosensitive resistor.

Figure 4:
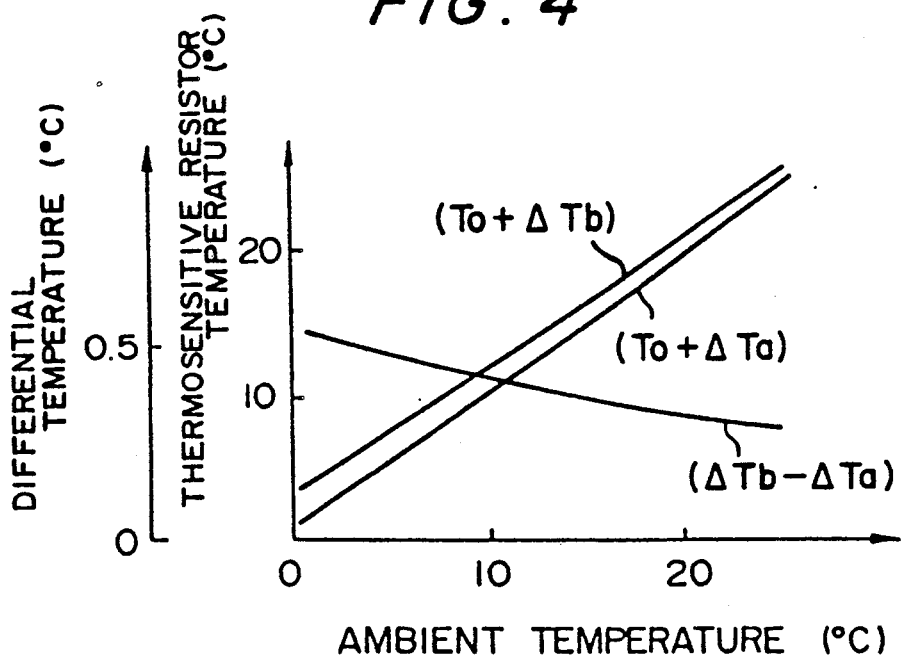
FIG. 4 is a characteristic curve graph showing the relation between the temperature or differential temperature and the resistance when no frost or dew exists around the thermosensitive resistors in the first embodiment.

The relation between an ambient temperature and a thermosensitive resistor temperature and the relation between an ambient temperature and a differential temperature of the thermosensitive resistors 548, 550, when the thermosensitive resistors 548, 550 are in air, namely, when no frost or dew exists around the thermosensitive resistors 548, 550, are shown in FIG. 4.

It is a common knowledge that the amount of heat radiation of a thermosensitive resistor varies sharply depending on whether the thermosensitive resistor is disposed in gas or it is disposed in solid or liquid. This is because the heat conductivity of solid is larger by two figures, compared with that of gas.

Now if the respective temperatures of the two thermosensitive resistors 548, 550 are compared to one another in air, the temperature of the one thermosensitive resistor 548 is $T_0+\Delta Ta$, and the temperature of the other thermosensitive resistor 550 is $T_0+\Delta Tb$. Therefore the differential temperature is $\Delta Tb - \Delta Ta$ as shown in FIG. 4. Here $T_0$ stands for air temperature.

Figure 5:
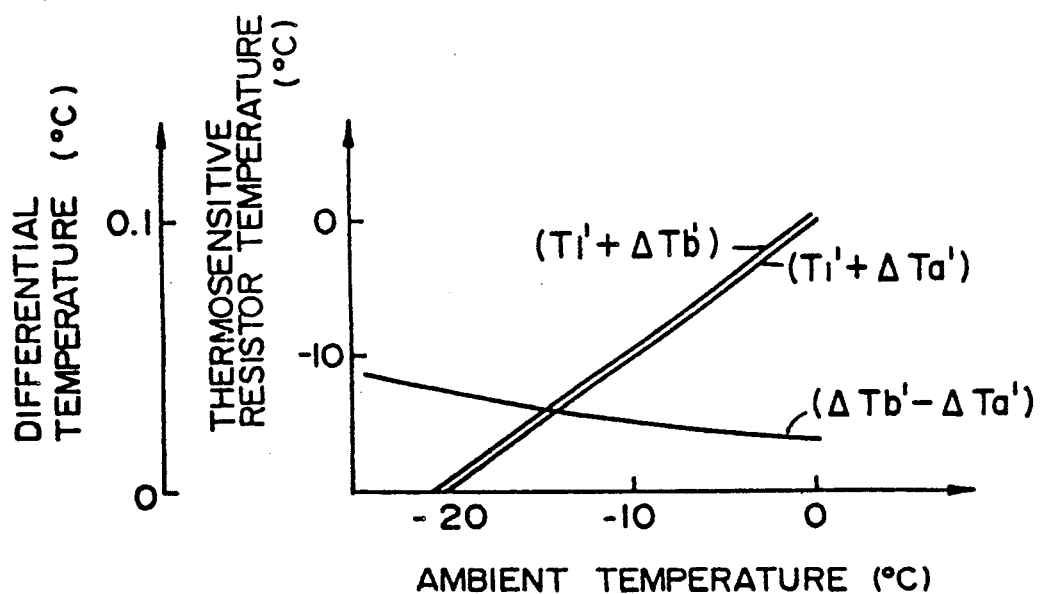
FIG. 5 is a characteristic curve graph similar to FIG. 4, showing the typical relation between the temperature or differential temperature and the resistance when frost or dew has developed over the thermosensitive resistors.

On the other hand, if the two thermosensitive resistors 548, 550 are located in water or ice (frost), their respective temperatures are $T_1+\Delta Ta'$ and $T_1'+\Delta Tb'$. Therefore the differential temperature is $\Delta Tb'-\Delta Ta'$ as shown in FIG. 5.

However, because the heat conductivity of water or ice is larger than that of air, $\Delta Ta' < \Delta Ta$ and $\Delta Tb' < \Delta Tb$. As a result, as shown in FIG. 5, the temperature $\Delta Tb'-\Delta Ta'$ is large enough in magnitude, compared to $\Delta Tb-\Delta Ta$ as shown in FIG. 4.

When the differential temperature between the two thermosensitive resistors 548, 550 is reduced to more than a predetermined extent, it can be regarded as a sign that the surfaces of thermosensitive resistors 548, 550 have been covered with frost or dew.

In FIG. 2, the operational amplifier 562 detects the respective temperatures of the two thermosensitive resistors 548, 550 to obtain a difference therebetween and then supplies this differential temperature value to one input terminal of the comparator 564.

To the other input terminal of the comparator 564, a reference voltage $Vref_2$, equivalent to the differential temperature between the two thermosensitive resistors 548, 550 when no frost or dew exists around the thermosensitive resistors 548, 550, is impressed. The comparator 564 thus makes a discrimination as to whether the output of the operational amplifier 562 is below the reference voltage value $Vref_2$.

According to the principles of this invention, yet when the surface of a thermosensitive resistor is covered with water (dew) instead of ice (frost), $\Delta Tb-\Delta Ta$ is small. Therefore, for detecting frost and dew distinctly of each other, a comparator 566 may be used to monitor an ambient temperature $T_0$ via the one thermosensitive resistor 548 which is at a temperature very close to the ambient temperature $T_0$ because the amount of current supplied to the thermosensitive resistor 564 is very small.

To the other input terminal of the comparator 566, a reference voltage $Vref_1$ equivalent to the freezing point of water is impressed from the direct-current source. When this input signal indicative of the monitored temperature from the thermosensitive resistor 548 is smaller than a reference voltage signal, it can be regarded as a sign that the surface of the thermosensitive resistor 548 has been covered with frost, not water.

When the detection signal of either comparator 564, 566 is below the reference value, a negative logic output is issued to take a logical operation AND by a pair of diodes $D_1$, $D_2$ which jointly constitutes a discriminator 568.

Only when the outputs of the two comparators 564, 566 meet, the transistor $Q_1$ is deenergized to stop the current flow from the power source $Ps_2$ to the ground.

Consequently a voltage is impressed to the base of the transistor $Q_2$ from the power source $Ps_2$ via the resistances $R_7$, $R_8$, and the transistor $Q_2$ is thereby energized to issue to a non-illustrated defroster drive unit, for example, an output signal giving a notice of the developing of frost. This output means: "the ambient temperature (i.e., temperature of the thermistor 12) is below 0° C., and the surfaces of the thermosensitive resistors are covered with ice (frost)".

The differential temperature $\Delta Tb - \Delta Ta$ varies depending on the state of ice covering over the thermosensitive resistors; by selectively varying the reference voltage of the comparator 564, it is possible to detect the developing of ice (frost) with maximum sensitivity.

If it is not necessary to distinguish between frost and dew when detecting, the comparator 566 and the diodes $D_1$, $D_2$ may be omitted.

In the foregoing embodiments, a thermistor is used for each thermosensitive resistor. However, this invention should by no means be limited to this specific form. The thermosensitive resistor may be a resistor made from platinum or nickel, for example, provided that the resistance-temperature coefficient of that resistor is positive.

Further, a control circuit employing a timer circuit or a microcomputer may be added in the arithmetic circuit.

In the illustrated embodiments, the arithmetic circuit is composed of a single operational amplifier, a pair of comparators, and transistors. Alternatively, the output voltage of the thermosensitive resistor may be inputted to an A/D converter and then may be processed as digital data with arithmetic operations by a microprocessor.

Figure 6:
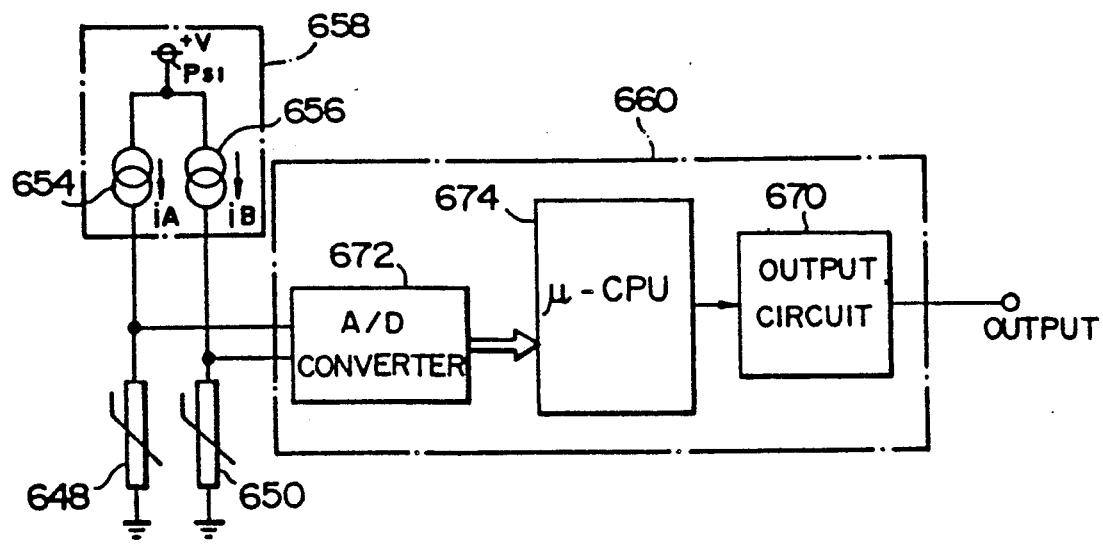
FIG. 6 is a block diagram of a modified sensor according to a second embodiment.

FIG. 6 is a block diagram showing a second embodiment having such an alternative construction. In this embodiment, a modified arithmetic circuit 660 is composed of an A/D converter 672 for converting the output currents of two thermosensitive resistors 648, 650 from analog form to digital form, a μ-CPU 674 for calculating a differential temperature between the thermosensitive resistors 648, 650 from digital data outputted from the A/D converter 672, and an output circuit 670 for outputting a frost-and-dew signal based on the output of the μ-CPU 674. The arrangement of this embodiment can offer the same result as that of the first embodiment.

Figure 7:
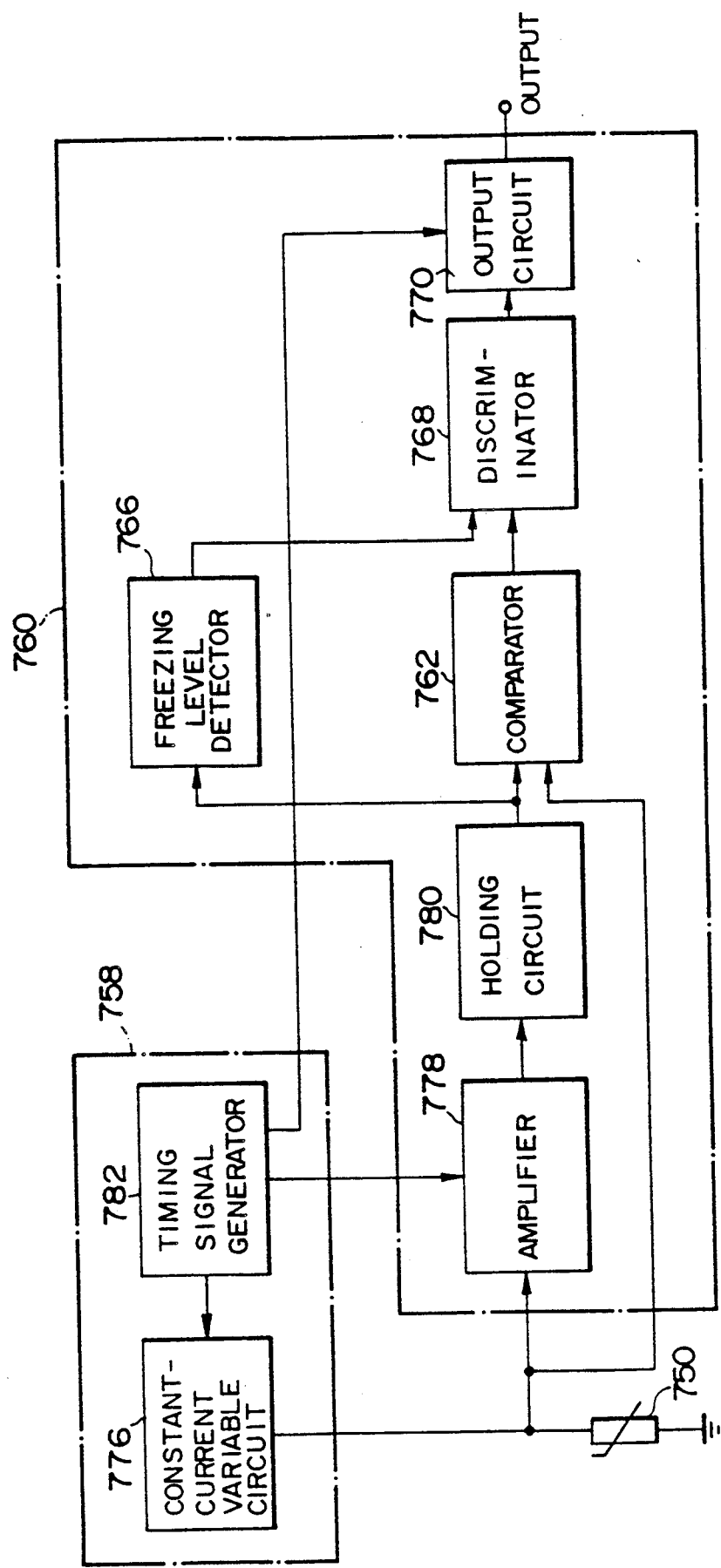
FIG. 7 is a block diagram of another modified sensor according to a third embodiment.

FIG. 7 shows a third embodiment, in which two different-value currents, i.e., a heat-generating current and a comparative reference current from a constant-current variable circuit 776 are alternately supplied to a single thermosensitive resistor 750 grounded at one end.

In the third embodiment, time-divided different currents $i_A$, $i_B$ are supplied to the single thermosensitive resistor 750, and the differential temperature is detected in terms of the different amounts of heat energy radiated when frost or dew exists around and when no frost or dew exists around. This detection is achieved by temporarily delaying one of the two output voltage values of the thermosensitive resistor 750 to meet with the detection timing signal of the other output voltage value for comparison.

Specifically, one of two alternately selective detection values is delayed and then supplied to the comparator circuit 762 at the same timing as the succeeding other detection value.

Here, since the heat-generating current $i_B$ is set at a value higher than the comparative reference current $i_A$, a deviation would be created therebetween during no developing of frost or dew if compared as they are. To meet the two values with each other, in this embodiment, the comparative reference current $i_A$ is amplified by an amplifier 778, when detecting the comparative reference current, up to a level equal to the detection value by the heat-generating current.

As is apparent from FIG. 7, the output of the thermosensitive resistor 750 is amplified by the amplifier 778, and then the amplified output is held for a predetermined period by a holding circuit 780 succeeding to the amplifier 778.

In this embodiment, this signal is held when the comparative reference current $i_A$ is supplied to the thermosensitive resistor 750, and the angle of amplification of the amplifier 778 can be given by the follwing equation:

$$a = _BR_0/i_AR_0 = i_B/i_A$$

Then the output of the amplifier 778 enters the holding circuit 780. Since two current values are sequentially impressed to this holding circuit 780 as described above, the voltages created at the thermosensitive resistor 750 by the two current values cannot be compared. For instance, the voltage created at the amplifier 778, when the current value $i_A$ is supplied, is temporarily held so that the comparator circuit 762 can compare this voltage with the voltage created at the thermosensitive resistor 750 by the supply of the current value $i_B$ after a predetermined period of time.

The comparator circuit 762 compares a differential temperature created when the currents $i_A$, $i_B$ are supplied to the thermosensitive resistor 750. On the other hand, to make a judgment on the developing of frost only, a freezing level detector circuit 766 parallel to the comparator circuit 762 discriminates whether the ambient temperature $T_0$ of the thermosensitive resistor 750 is below 0° C., which causes frost to develop.

To the output circuit 770 serving as the output means for the constant-current variable circuit 776, the amplifier 778 and the arithmetic circuit 760, the timing signal generator circuit 782 supplies a signal to alternately change over the current values between $i_A$, $i_B$ to be supplied to the thermosensitive resistor 750, another signal to do that change-over in response to the last-named signal, and still another signal to do the output control, each signal at a predetermined period.

If the temperature increase is below a reference value, a discriminator 768 judges it as a sign of the developing of frost or dew, based on the output of the comparator circuit 762. To detect the developing of frost only, it requires an additional condition that an ambient temperature $T_0$ is below 0° C.

Figure 8:
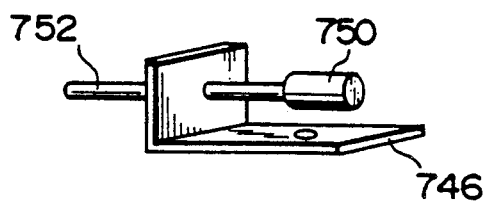
FIG. 8 is a perspective view showing a partial appearance of the sensor of the third embodiment.

FIG. 8 shows the perspective appearance around the thermosensitive resistor 750 in the practical sensor of FIG. 7. In FIG. 8, the thermosensitive resistor 750 is carried on a distal end of a shaft 752 extending through a side wall of a base 746 in the form of an angled or hook-shaped plate.

Figure 9:
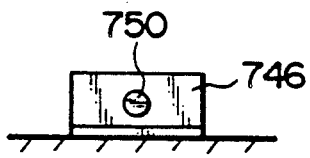
FIG. 9 is a side elevational view of FIG. 8, showing the sensor with no frost or dew around.
Figure 10:
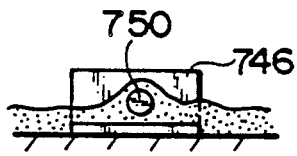
FIG. 10 is a view similar to FIG. 9, showing the sensor having been covered with frost or dew.

With no frost or dew around, as shown in FIG. 9, the thermosensitive resistor 750 is located in air. With frost or dew around, as shown in FIG. 10, the surface of the thermosensitive resistor 750 is covered with frost or dew.

Figure 11:
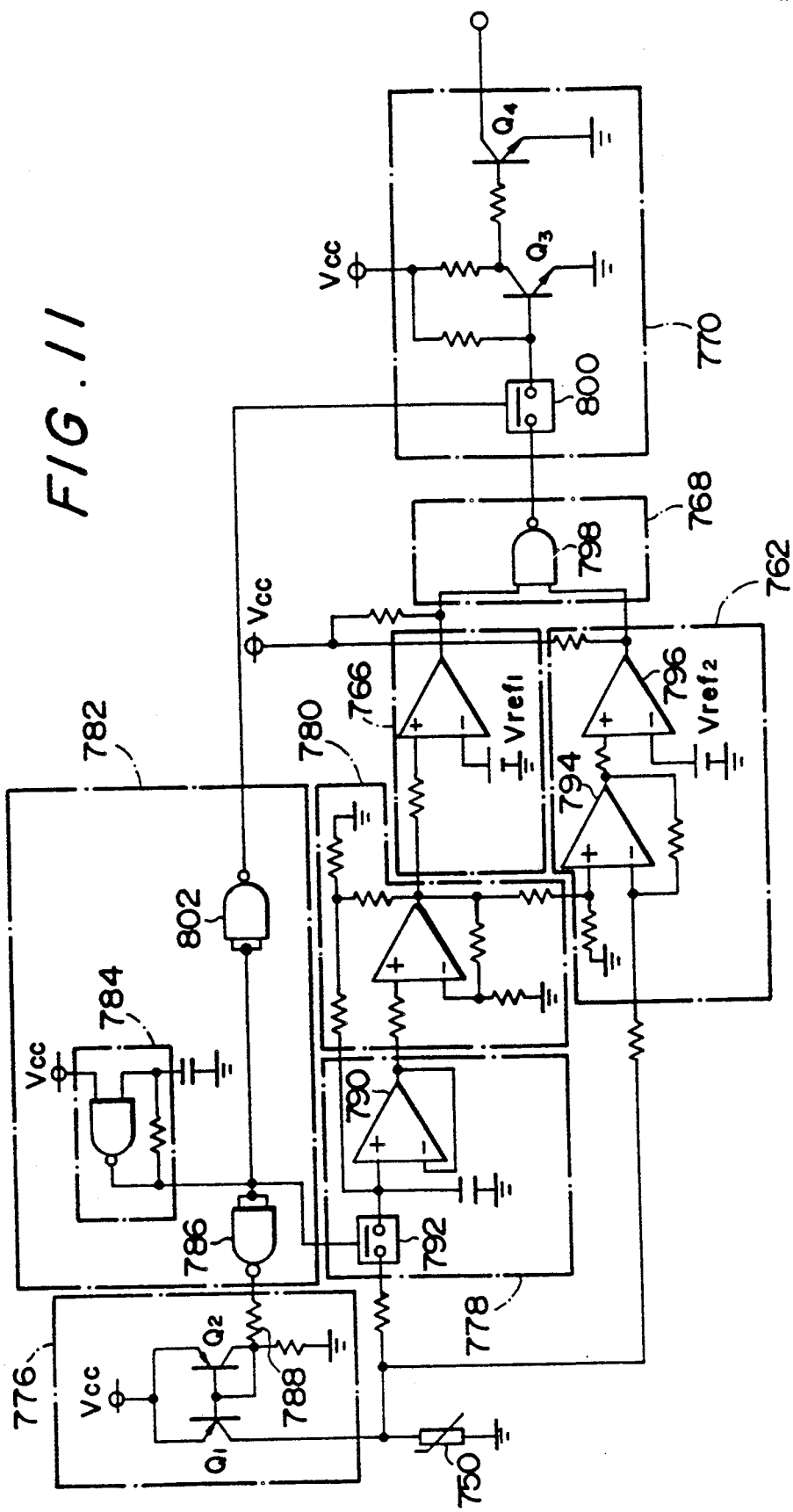
FIG. 11 is a detail circuit diagram corresponding to FIG. 7.
Figure 13:
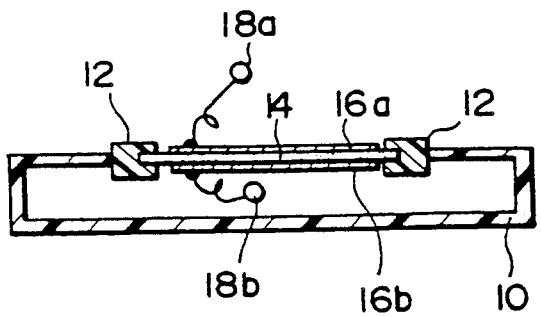
FIG. 13 is a cross-sectional view of a prior art sensor for detecting frost or dew by the change in oscillation frequency of an piezo-electric resonator.
Figure 14:
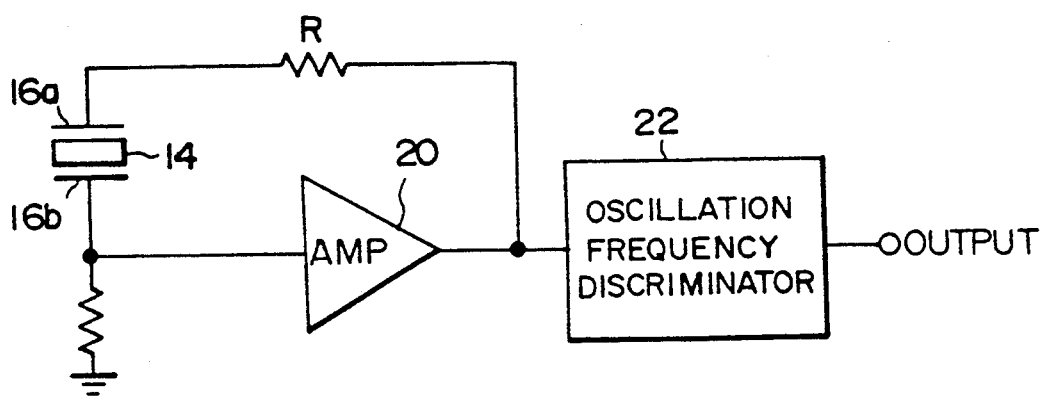
FIG. 14 is a circuit diagram of the sensor of FIG. 13.
Figure 15:
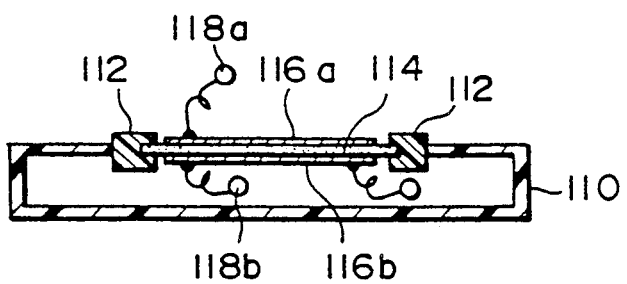
FIG. 15 is a view similar to FIG. 13, showing another prior art sensor for detecting frost or dew by the change in oscillation amplitude of a piezoelectric resonator.
Figure 16:
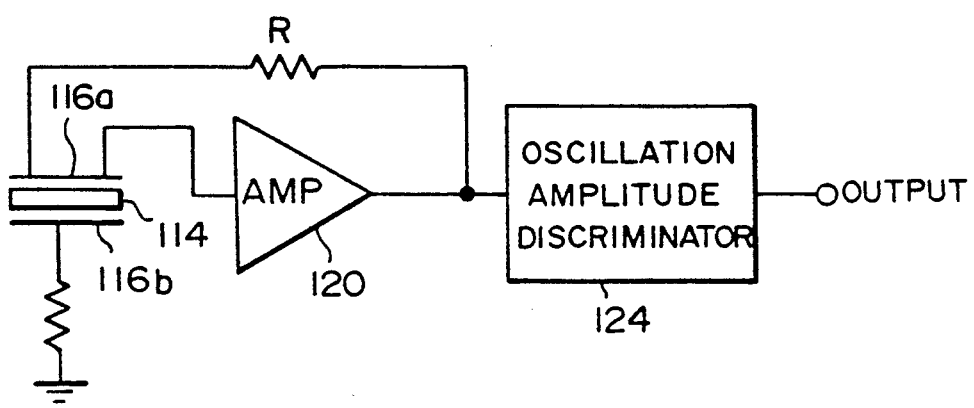
FIG. 16 is a circuit diagram of the sensor of FIG. 15.
Figure 17:
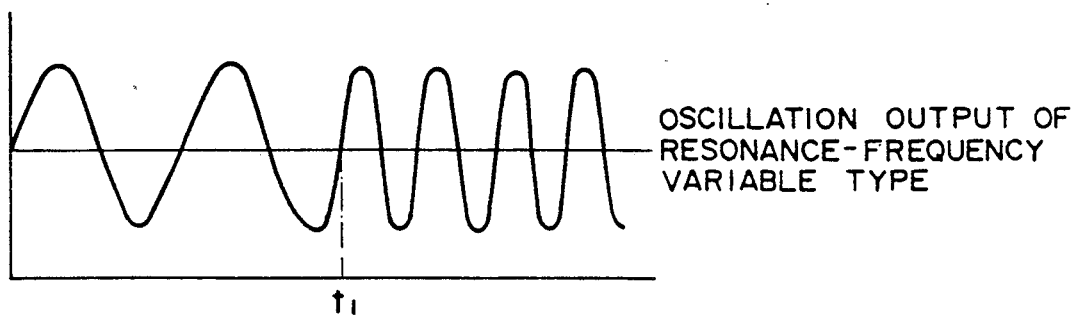
FIG. 17 is a wave-form graph showing the oscillation output of the sensor of FIG. 13.
Figure 18:
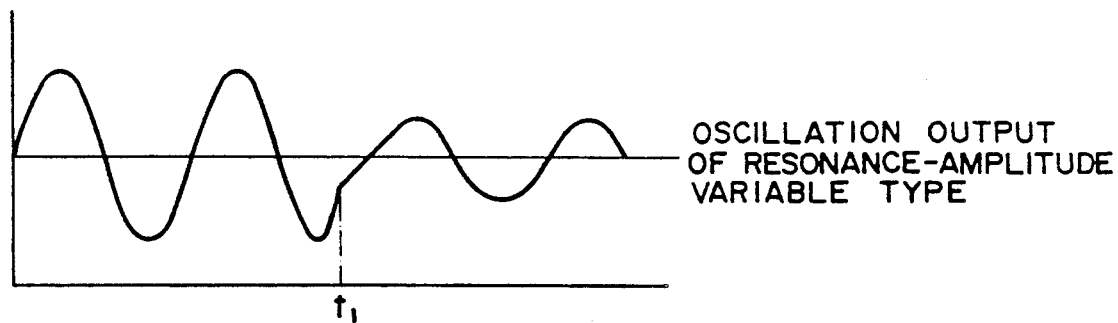
FIG. 18 is a wave-form graph similar to FIG. 17, showing the oscillation output of the sensor of FIG. 15.
Figure 19:
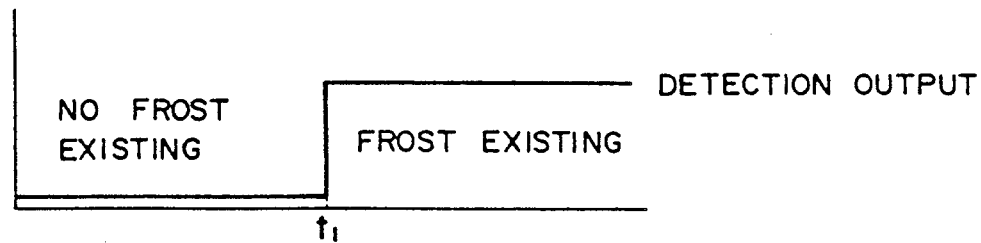
FIG. 19 is a detection output graph corresponding to FIGS. 17 and 18, showing the presence/absence of frost or dew.
Figure 20:
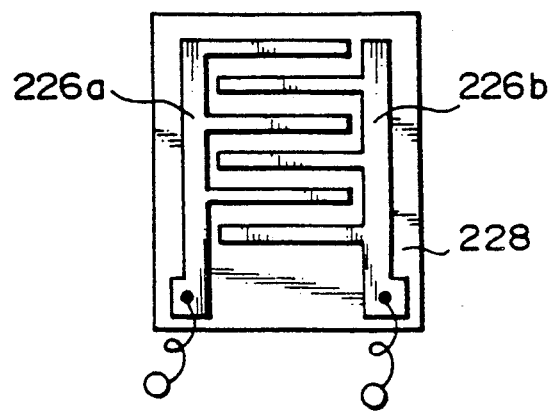
FIG. 20 is a plan view of still another prior art sensor in which frost or dew is detected in terms of the change in dielectric factor.
Figure 21:
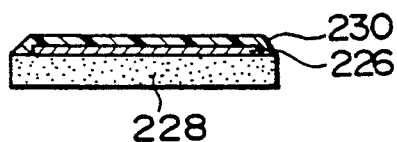
FIG. 21 is a perspective view of the sensor of FIG. 20.
Figure 22:
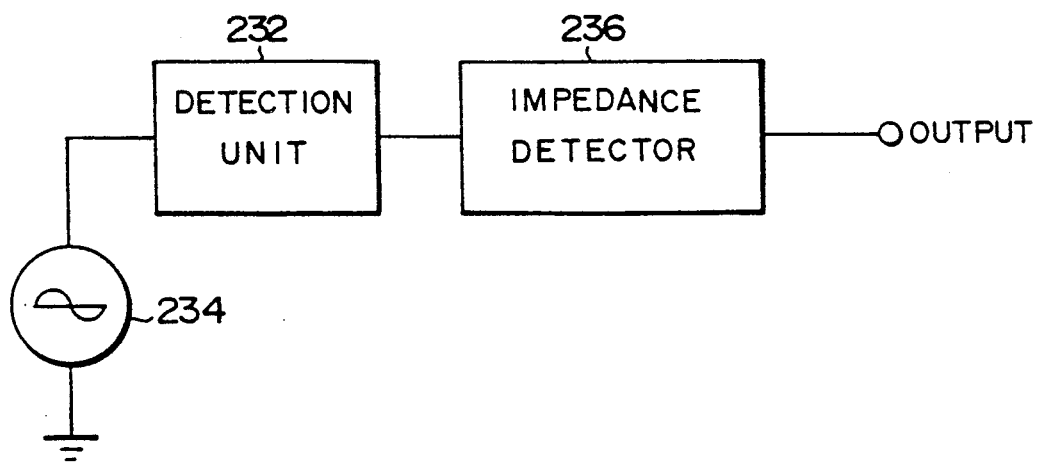
FIG. 22 is a block diagram showing a circuit of the sensor of FIG. 20.
Figure 23:
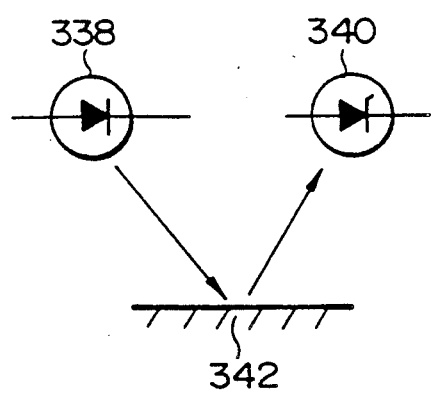
FIGS. 23 and 24 are schematic diagrams of two other kinds of prior art sensors, showing the structure and the principle of operation of the individual sensor in which frost or dew is detected in terms of the change of amount of light reaching a photodiode from an LED.
Figure 24:
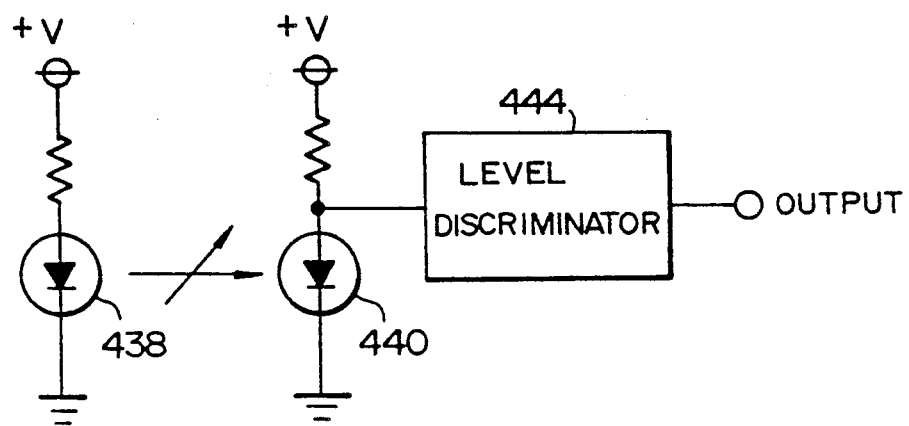

The operation of the sensor of FIG. 7 (third embodiment) will now described in greater detail with reference to FIG. 11 showing a practical circuit.

In FIG. 11, to the thermosensitive resistor 750, a comparative reference current $i_A$ and a heat-generating current $i_B$ are alternately supplied at chronologically different timings from the constant-current variable circuit 776 which is composed of the transistors $Q_1$, $Q_2$.

To make a change-over on the constant-current variable circuit 776, the sensor is equipped with a timing circuit 782. In the illustrated embodiment, the timing circuit 782 includes an oscillator 784 and a gate 786; the respective supply timings of the two current values $i_A$, $i_B$ are alternately changed over in an oscillation period of the oscillator 784.

The oscillator 784 supplies an oscillation output from the gate 786 to the collector of each of the transistor $Q_1$, $Q_2$ via a resistance 788. When the output of the oscillator 784 is "L" level, the current flowing to the collector of the transistor $Q_2$ via the resistance 788 increases. At that moment, since the transistors $Q_1$, $Q_2$ jointly constitute a so-called current mirror, the initial current value $i_A$ increases to reach the heat-generating current $i_B$ as the current $i_A$ flows through the collector of the transistor $Q_2$.

The output side of the thermosensitive resistor 750 is connected to the negative input side of the comparator circuit 762, as described above; when the comparative reference current $i_A$ is supplied to the thermosensitive resistor 750, then its output is supplied to the amplifier 778.

The amplifier 778 is composed of an amplifier circuit 790 and a switch 792 disposed immediately upstream of the amplifier circuit 790. When the output of the oscillator 784 is "L" level, the timing circuit 782 issues a change-over signal to open the switch 792.

Accordingly, the amplifier 778 can fetch the output of the thermosensitive resistor 750 only when the comparative reference current $i_A$ is supplied to the thermosensitive resistor 750.

The output of the amplifier 778 is supplied to the holding circuit 780, and the output of the holding circuit is supplied to the positive input terminal of the comparator 762.

Thus the comparator 762 makes a delay, by the holding circuit 780, of one of the outputs of the thermosensitive resistor 750, when the comparative reference current $i_A$ and the heat-generating current $i_B$ are supplied to the thermosensitive resistor 750 at the chronologically different timings, to meet the respective timings for comparison.

In the amplifier 778, its amplification constant is set such that the signal values to be supplied to the comparator 762 are identical when no frost or dew exists around the thermosensitive resistor 750. Consequently the output of the comparator 762 is 0 (zero) during no developing of frost or dew.

On the contrary, when frost or dew develops over the surface of the thermosensitive resistor 750, the negative input value of the comparator circuit 762 descends. A signal corresponding to the difference in temperature increase due to the heat-generation is supplied from a first comparator 794 to a second comparator 796 where the output value of the first comparator 794 is compared with a reference value. Then from the second comparator 796, a frost-and-dew signal is outputted when the difference in temperature increase due to heat radiation is over a predetermined value.

Thus in this embodiment, the sensor is also equipped with a freezing level detector circuit 766 to obtain a signal when frost has develops over the thermosensitive resistor 750. In the freezing level detector circuit 766, the output of the holding circuit 780, namely, the output of the thermosensitive resistor 750 during supplying the comparative reference current $i_A$ is compared with the reference value. When the ambient temperature (thermistor) descends below 0° C., then the frost signal is outputted.

Further, these two detection signals take their AND output by the discriminator circuit 768 including the gate 798, and are then supplied to a non-illustrated processing circuit via the output circuit 770.

Here, during the comparative reference current $i_A$ is being supplied to the thermosensitive resistor 750, the negative input value of the first comparator 794 is lower than the positive input value by $1/\alpha$. This difference is outputted to the first comparator 796, which might cause an error frost-and-dew signal.

A switch 800 is connected to the output side of the discriminator 768. To this switch 800, a timing signal is supplied from the oscillator 784 in the timing circuit 782 via a gate 802 built in the timing circuit 782. By releasing the switch 800 when the comparative reference current $i_A$ flows to the thermosensitive resistor 750, it is possible to avoid such a misoperation.

Connected to the downstream side of the switch 800 are two transistors $Q_3$, $Q_4$, which constitute, jointly with the switch 8000, the output circuit 770. Vcc is connected to the collector and base of each of the two transistors $Q_3$, $Q_4$. These transistors $Q_3$, $Q_4$ serve to amplify the output of the discriminator 768 and deliver this amplified output as a frost-and-dew notifying signal to a subsequent processing circuit.

In this illustrated embodiment, the principles of this invention is applied for the purpose of detecting frost only. Alternatively, by omitting or modifying each of the foregoing threshold levels, it is possible to detect both frost and dew, or only dew.

According to this embodiment, partly since the thermosensitive resistor used as a frost and dew detecting means is hardly subjected to the exterior force or vibration, and partly since the thermosensitive resistor is inexpensive and small-sized and has an excellent mechanical strength, it is possible to detect the developing of frost or dew with very high reliability.

Figure 12:
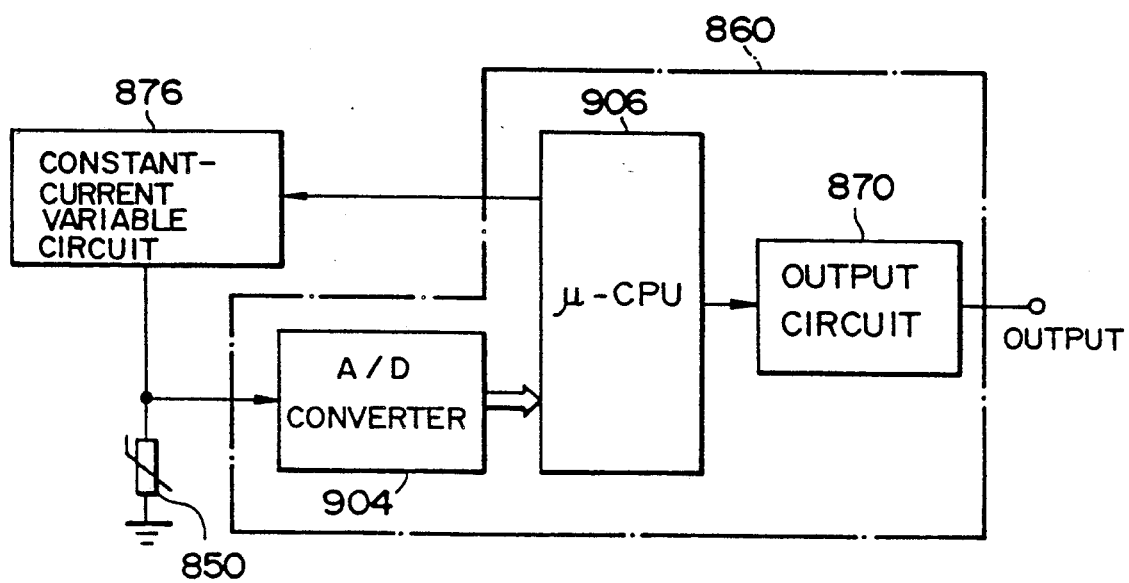
FIG. 12 is a block diagram showing still another modified sensor according to a fourth embodiment.

FIG. 12 shows a fourth embodiment, in which an output port signal of a $\mu$-CPU 906, instead of the oscillation circuit, is used to instruct the constant-current variable circuit 876 to change over the current to be supplied to the thermosensitive resistor 850. The detected temperature signal from a thermosensitive resistor 850 is digitalized by an A/D converter 904 and is then processed in the $\mu$-CPU 906. The result of arithmetical operation in the $\mu$-CPU 906 is outputted as a frost-and-dew signal from an output circuit 870.

Apart from the arithmetical operation of the detection signals, this embodiment is identical in the basic principle of frost and dew detection with the third embodiment, giving the similar result.

To sum up the foregoing description, according to the first and second embodiments, partly because a pair of thermosensitive resistors is used as a frost and dew detecting means, and partly because the change of a differential temperature between the thermosensitive resistors is used as a parameter for the arithmetical operation, occurrence of misdetection due to any outside force or vibration can be reduced to a minimum, thus guaranteeing an inexpensive frost and dew sensor which offers a very reliable performance and has an adequate mechanical strength.

According to the third and fourth embodiments, partly since a heat-generating current and a comparative reference current are alternately supplied to a single thermosensitive resistor such as a thermistor to create a differential temperature, and partly since the developing of frost or dew is detected in terms of the reduced differential temperature due to the action of heat conducting when frost or dew has developed over the surface of the thermosensitive resistor, it is possible to achieve an improved frost and dew sensor which is small-sized, durable and inexpensive and offers an reliable detection performance. Further, sensible detection of frost and dew can be achieved without causing any misoperation due to the outside force or vibration.

What is claimed is:

1. A frost and dew sensor comprising:
   (a) a thermosensitive resistor capable of generating heat by itself due to a given current supplied thereto, said thermosensitive resistor having a resistance varying according to the change of temperature of said thermosensitive resistor;
   (b) a power source for changing the temperature of said thermosensitive resistor periodically, said power source including a variable constant-current source for alternately supplying a heat-generating current and a comparative reference current to said thermosensitive resistor, said comparative reference current being such that it causes a temperature increase of said thermosensitive resistor to only a negligible extent with respect to the temperature increase due to the heat-generating current; and
   (c) an arithmetic circuit for fetching a temperature of said thermosensitive resistor as an output voltage according to a resistance corresponding to the temperature and for generating a frost-and-dew signal according to a difference between the output voltage during the heat-generating current is being supplied to said thermosensitive resistor and the output voltage during the comparative reference current is being supplied to said thermosensitive resistor, whereby the frost-and-dew signal is issued as presumed that said thermosensitive resistor is covered with frost or dew when a differential temperature of said thermosensitive resistor in such two durations is lowered.

2. A frost and dew sensor according to claim 1, wherein said arithmetic circuit includes:
   an amplifier for amplifying the output voltage of said thermosensitive resistor, during the comparative reference current is being supplied thereto, at a rate corresponding to a ratio of the heat-generating voltage to the comparative reference current to output the amplified output voltage;
   a holding circuit for holding the output of said amplifier to output the same output with a delay for the duration the comparative reference current is being supplied to said thermosensitive resistor; and
   a comparator circuit for first comparing the output of said holding circuit with the output voltage of said thermosensitive resistor, during the heat-generating current is being supplied, to find a differential temperature of said thermosensitive resistor between the temperature during the comparative reference current is being supplied and that during the heat-generating current is being supplied, and for secondly comparing the differential temperature with a predetermined reference value.

3. A frost and dew sensor according to claim 1, wherein said arithmetic circuit includes:
   an A/D converter for converting the output voltage of each said thermosensitive resistor into digital data;
   a $\mu$-CPU for performing a predetermined arithmetical operation with respect to the digital data, outputted from said A/D converter, to find a differential temperature at said thermosensitive resistors; and
   an output circuit for generating and outputting a frost-and-dew signal according to the arithmetic result of said $\mu$-CPU.

4. A frost and dew sensor according to claim 2, wherein said comparator circuit includes:
   a first comparator for comparing the output signal of said thermosensitive resistor, during the heat-generating current is being supplied, with the output of said holding circuit to find the difference between the two outputs; and
   a second comparator for comparing the output signal of said first comparator with a reference value.

5. A frost and dew sensor according to claim 4, wherein said arithmetic circuit includes a freezing level detector circuit for comparing the output current of said thermosensitive resistor corresponding to the comparative reference current with a predetermined freezing level reference value to detect whether an ambient temperature of said thermosensitive resistor is below the freezing point.

6. A frost and dew sensor according to claim 5, wherein said arithmetic circuit includes a discriminator for comparing the output signal of said comparator circuit with the output signal of said freezing level detector circuit to discriminate whether said thermosensitive resistor is covered with frost, when the ambient temperature of said thermosensitive resistor is below the freezing point.

7. A frost and dew sensor according to claim 6, wherein said arithmetic circuit includes an amplifier for amplifying the output of said discriminator to output the amplified output;
   said power source including an oscillator for producing an alternate timing to alternate the output of said variable constant-current source between the comparative reference current and the heat-generating current, said oscillator including a timing circuit for supplying a control signal to said amplifier according to the alternate timing produced by said oscillator and also for supplying the same control signal to said output circuit according to the same alternate timing;
   said amplifier circuit including a switch adapted to be energized and deenergized by said timing circuit in such a manner that the output current of said thermosensitive resistor is inputted only during the comparative reference current is being supplied to said thermosensitive resistor; and
   said output circuit including another switch adapted to be energized and deenergized by said timing circuit in such a manner that the output of the frost-and-dew signal to the exterior is prohibited during the comparative reference current is being supplied to said thermosensitive resistor.

8. A frost and dew sensor according to claim 7, further including a shaft carrying thereon said thermosensitive resistor, and a base supporting said shaft, said thermosensitive resistor being a thermistor.

* * * * *